US006334844B1

United States Patent
Akiba

(12) United States Patent
(10) Patent No.: US 6,334,844 B1
(45) Date of Patent: Jan. 1, 2002

(54) MECHANICAL- AND ELECTRICAL-MODE CHANGEABLE ENDOSCOPE CONDUIT CONTROLLER

(75) Inventor: Haruo Akiba, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/637,635

(22) Filed: Aug. 14, 2000

(30) Foreign Application Priority Data

Aug. 17, 1999 (JP) .......................................... 11-230289
Aug. 27, 1999 (JP) .......................................... 11-241154

(51) Int. Cl.[7] .............................................. A61D 1/015
(52) U.S. Cl. ...................................... 600/159; 600/156
(58) Field of Search ................................ 600/156–159; 604/30, 33

(56) References Cited

U.S. PATENT DOCUMENTS 4,982,726 A 1/1991 Taira
5,386,817 A * 2/1995 Jones .......................... 600/159
5,891,014 A 4/1999 Akiba

FOREIGN PATENT DOCUMENTS

DE 34 15 837 11/1984

* cited by examiner

Primary Examiner—John Mulcahy
(74) Attorney, Agent, or Firm—Snider & Associates; Ronald R. Snider

(57) ABSTRACT

An endoscope conduit controller makes it possible to selectively use both fluid control by a mechanical valve and fluid control by a solenoid-valve unit in one system. The controller is constituted so that both a mechanical suction member and an electrical suction member having a solenoid-valve opening/closing switch can be removably set to a catching port of a catching part provided for a case body of an endoscope operation part. Moreover, the controller is configured so that an operation signal of the electrical suction member is transmitted to a solenoid-valve unit by electrical connection unit set in an endoscope or through an external signal cable or the like. Furthermore, the same is true for the case of air supply/water supply. Thereby, it is possible to selectively perform fluid control by a mechanical valve or fluid control by a solenoid-valve unit in one endoscope.

6 Claims, 9 Drawing Sheets

MECHANICAL- AND ELECTRICAL-MODE CHANGEABLE ENDOSCOPE CONDUIT CONTROLLER

BACKGROUND OF THE INVENTION

1. Field of the Invention

The present invention relates to an endoscope conduit controller for supplying air or water to the front end through an air-supply or water-supply tube or for absorbing the content of an observation object from the front end through a suction tube.

2. Description of the Prior Art

An endoscope makes it possible to jet air or water (physiological saline or the like) from an air-supply or water-supply nozzle at the front end toward an observation window or the like or absorbing the content or the like of an observation object through a forceps port at the front end. Therefore, an air-supply tube, water-supply tube, and suction tube are set in the endoscope and moreover, a mechanical operation valve or electrical operation switch for controlling flows in these conduits is set in the endoscope.

That is, flows in endoscope conduits have been controlled so far by a mechanical operation valve or a solenoid-valve unit and an operation switch. At the time of using the above described mechanical operation valve, a suction tube is opened or closed by moving a piston which one communication path is formed upward or downward in case of suction. Air is supplied by closing an atmosphere-release path of a piston on which two communication paths such as an air supply path including an atmosphere-release path and a water supply path are formed and water is supplied by pressing the piston downward.

The mechanical operation valve has an advantage that a flow rate can be finely controlled (analogously controlled) by changing pressed distances of a piston by a finger but it has a disadvantage that it is difficult to clean a valve part having a movable piston.

However, the solenoid-valve unit is set separately from the endoscope and an electrical operation switch for operating a solenoid valve in the solenoid-valve unit is set to an operation part. Attraction is performed by operating a relevant solenoid valve by turning on/off a suction switch. Air is supplied by pressing an air-supply/water-supply switch at first stage, for example, thereby operating a relevant solenoid valve and water is supplied by pressing the switch at second stage.

The solenoid-valve unit has an advantage that the valve part can be easily cleaned because the movable piston used for the mechanical operation valve is not used and thereby, the cleanability is improved.

BRIEF SUMMARY OF THE INVENTION

Object of the Invention

An endoscope conduit controller using the above mechanical operation valve or solenoid-valve unit has advantages and disadvantages. Therefore, selection of an endoscope depends on an applied portion or user's conditions and endoscope conduit controllers using the valve and unit are simultaneously used. At the time of inversely considering the above described, if it is possible to use the both types of controllers for one system, either of the both types can be selected depending on an applied portion or condition and the utility value is improved.

However, in case of conventional endoscopes, there is no compatibility between an endoscope using a mechanical operation valve and an endoscope using a solenoid-valve unit. That is, an endoscope is configured by an endoscope part serving as a scope, a light source unit or processor unit having a fluid supply part such as a pump, and a solenoid-valve unit. However, it is impossible to use an endoscope having an electrical operation switch for operating a solenoid-valve unit by connecting it to a light source unit or processor unit adopting a mechanical operation valve.

Moreover, there is a request of changing an endoscope to which a mechanical operation valve is applied currently used to an endoscope using a solenoid-valve unit. In this case, it is convenient to use an endoscope currently owned as an endoscope for a solenoid-valve unit without purchasing a new endoscope for a solenoid-valve unit if possible.

The present invention is made to solve the above problems and its object is to provide an endoscope conduit controller capable of properly obtaining advantages of a mechanical valve and a solenoid-valve unit in one system by selectively executing the fluid control by the mechanical valve and the fluid control by the solenoid-valve unit and securing compatibility between component units produced so as to have control modes different from each other.

SUMMARY OF THE INVENTION

To attain the above described object, the present invention comprises a mechanical operation member for controlling the flow of a fluid in an endoscope conduit with a mechanical valve configuration, an electrical operation member for controlling the flow of the fluid in the same conduit with an electrical switch, an operation-member catching part in which the conduit is extended and which makes it possible to selectively set or remove the mechanical and electrical operation members, and electrical connection means (circuit) for electrically connecting the electrical switch to the electrical operation member when the body is set to the operation-member catching part.

According to the present invention, when a mechanical operation member is set to an operation-member catching part, a conduit is opened or closed by pressing a mechanical operation member as ever by pressing the mechanical operation member and a flow rate can be also adjusted in accordance with a pressing degree of the operation member. Moreover, when an electrical operation member is set, an internal electrical switch is electrically connected with the body and simultaneously the conduit is also connected so that a fluid can be circulated. Then, by pressing the operation member, a solenoid valve operates and the conduit is opened or closed, and the flow rate is adjusted.

Moreover, another aspect of the present invention comprises a mechanical operation member, a catching part of the mechanical operation member, an electrical operation member constituted so as to be removable from the catching part to secure the flow of a fluid in a conduit and control the flow with an electrical switch, and signal transmission means for inputting an operation signal of the electrical operation member to an electrical fluid-supply part through the outside of an endoscope. The signal transmission means can use an external electrical-signal cable passing through the outside or a signal transmission structure using radio waves or light.

According to the above another aspect of the present invention, by setting an electrical operation member to a catching part from which a mechanical operation member is removed and connecting an external-signal-cable connector serving as electrical connection means to a solenoid-valve unit, a conventional mechanical-valve endoscope can be used as a solenoid-valve endoscope without changing configurations of the mechanical-valve endoscope.

DETAILED DESCRIPTION OF THE PREFERRED EMBODIMENTS

First Embodiment

Figure 3:
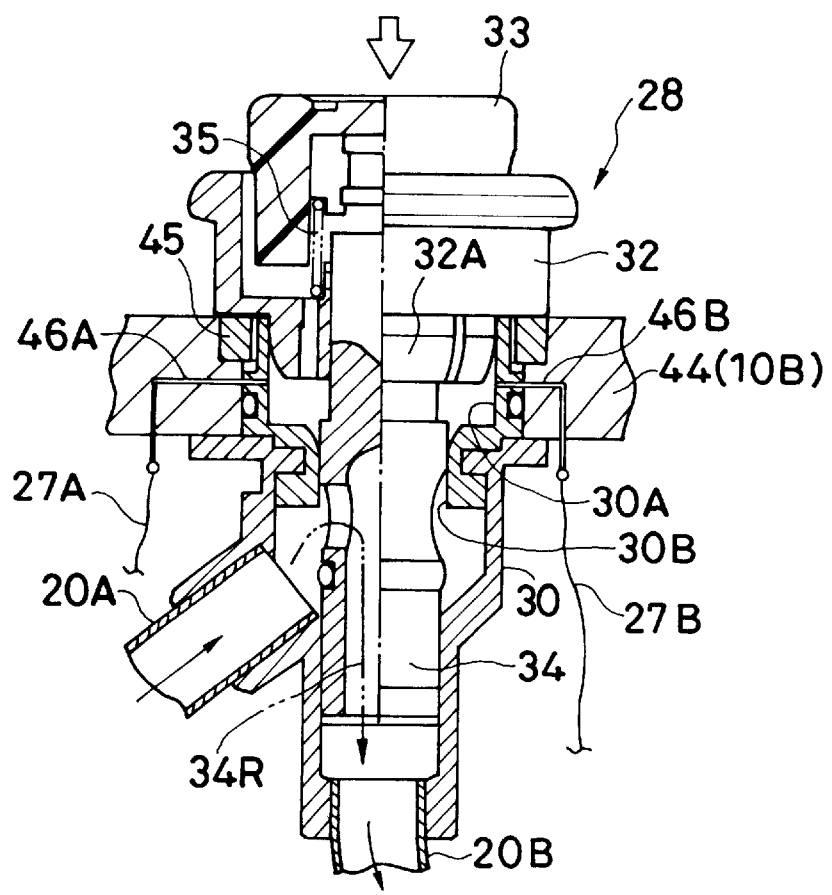
FIG. 3 is a sectional view showing a state of setting the mechanical suction member in FIG. 1 to the catching part (a state of pressing a piston)
Figure 4:
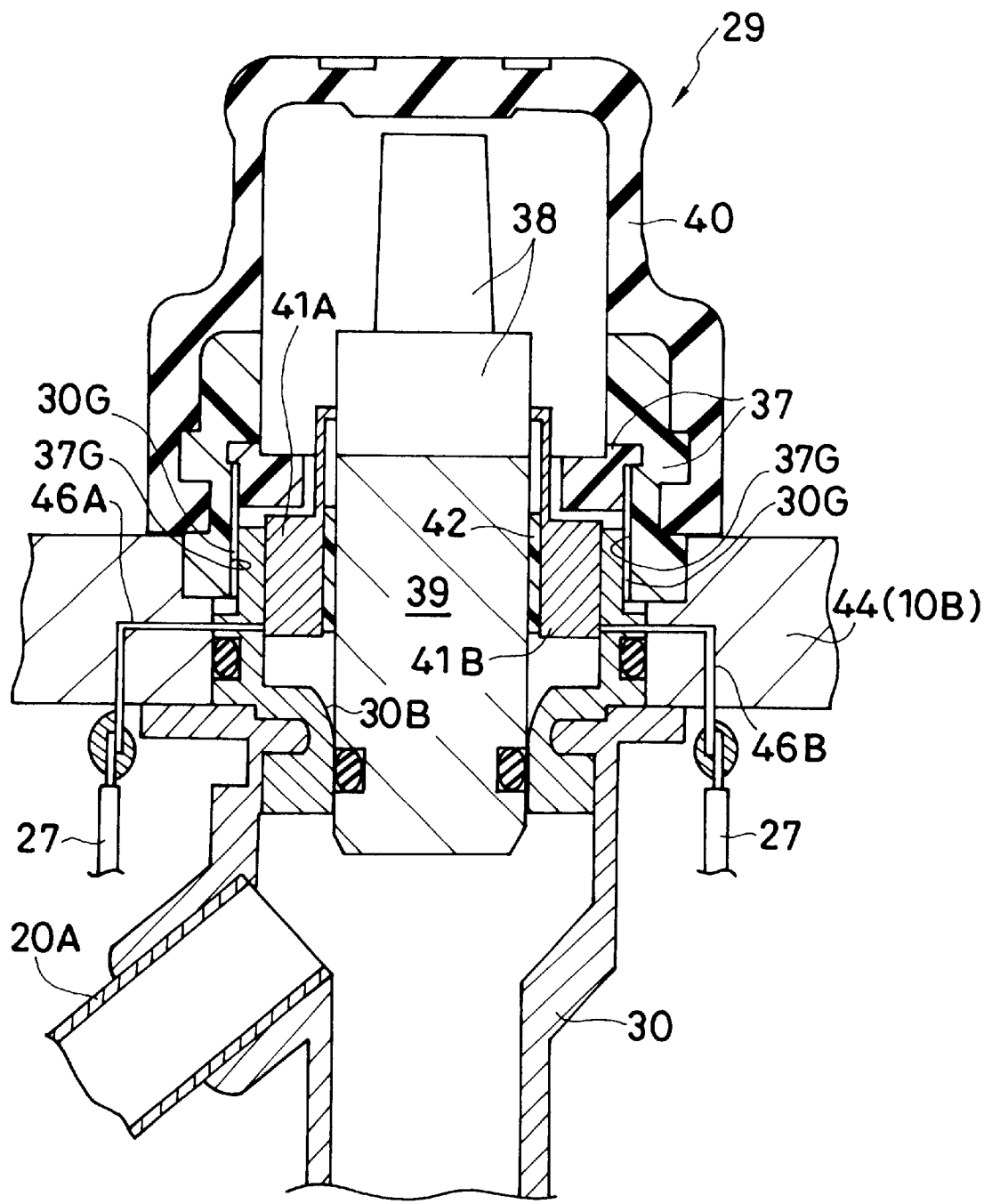
FIG. 4 is a sectional view showing a state of setting the electrical suction member in FIG. 1 to the catching part.
Figure 5:
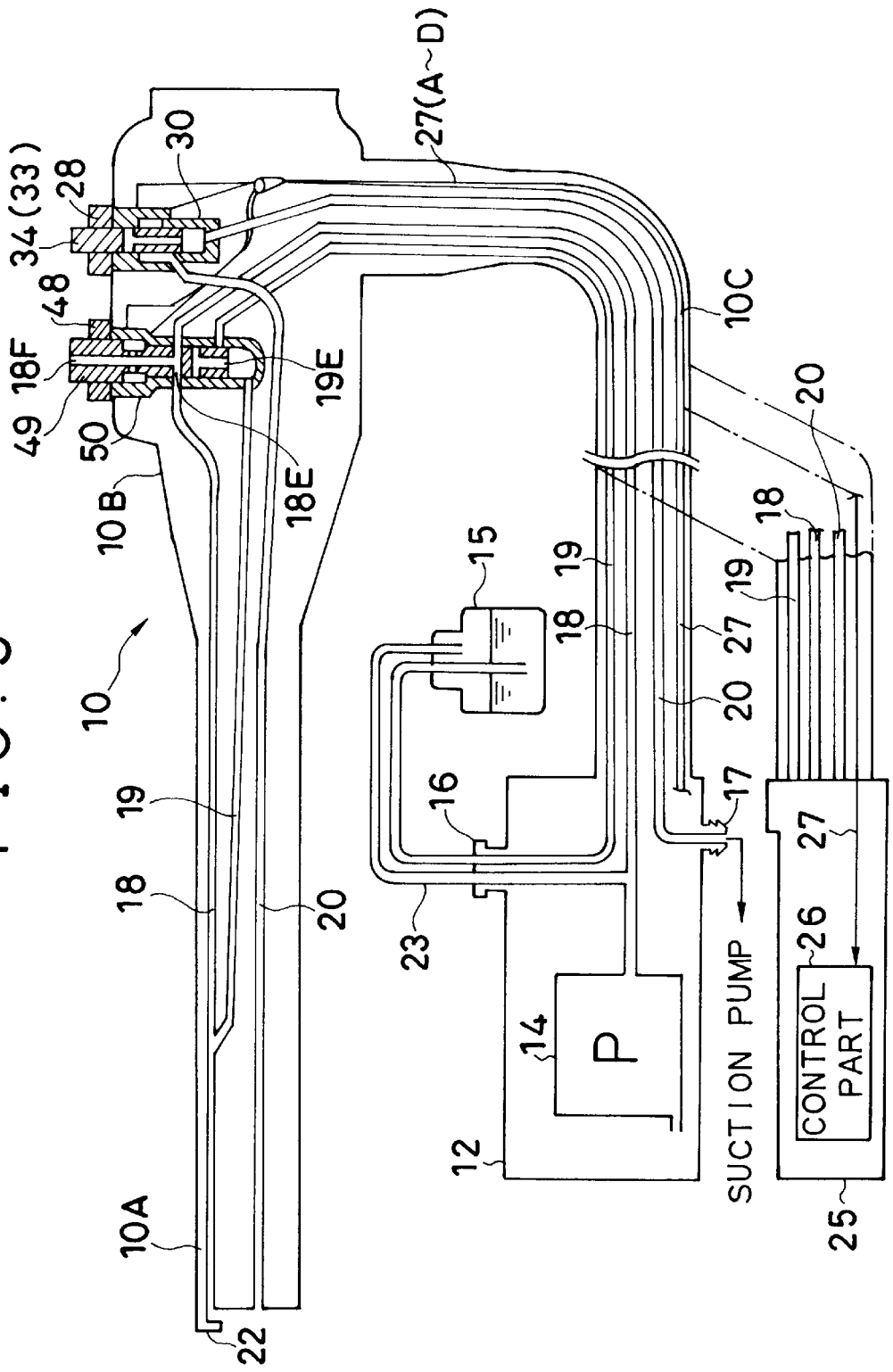
FIG. 5 is an illustration showing the general configuration of the endoscope of the first embodiment at the time of setting a mechanical operation member.

FIGS. 1 to 7 show configurations of the endoscope conduit controller of a first embodiment, in which FIG. 5 shows the general configuration of the controller to which a mechanical valve is applied. In FIG. 5, an endoscope (or electronic endoscope) 10 is configured by an insertion part 10A, an operation part 10B, and a cable part 10C, in which the cable part 10C is through connectors connected to an external unit 12 having a fluid supply part for a mechanical valve. The external unit 12 is configured by a light source unit, a processor, and a processor having a light-source unit. As illustrated, a pump (air-supply pump) 14, a conduit and connection port 16 to be connected to a water-supply tank 15, and a conduit and connection port 17 to be connected to a suction pump are included.

In case of the controller, an air-supply tube 18, a water-supply tube 19, and a suction tube 20 are used as endoscope conduits. The air-supply tube 18 and water-supply tube 19 are united into one tube at the front end of the insertion part 10A and a nozzle 22 for jetting a fluid to an observation window is set to the exit of the air-supply/water-supply tube. Moreover, the water-supply tube 19 is extended to the water-supply tank 15 at the external unit-12 side and an air-supply tube 23 is set between the water-supply tank 15 and pump 14.

Moreover, instead of the external unit 12, the cable part 10C of the endoscope 10 is constituted so as to be able to also connect with a solenoid-valve unit 25. The solenoid-valve unit 25 has connection ports to an air-supply pump, a water-supply pump, and a suction pump similarly to the case of the external unit 12 and is provided with a solenoid valve (pinch valve or diaphragm valve) for opening/closing conduits 18 to 20 and a control part 26 so that operations such as air supply, water supply, and suction can be performed by opening/closing the solenoid valve by the control part 26.

Moreover, an operation member making it possible to operate both a mechanical operation member (valve) and an electrical operation member (switch) is set to the endoscope operation part 10B. To transmit an operation signal when the electrical operation member is set, signal lines 27 (A to D) are extended from the operation part 10B up to the control part 26 of the solenoid-valve unit 25 through the cable part 10C. FIG. 5 shows a state when a mechanical operation member is set.

Figure 1A:
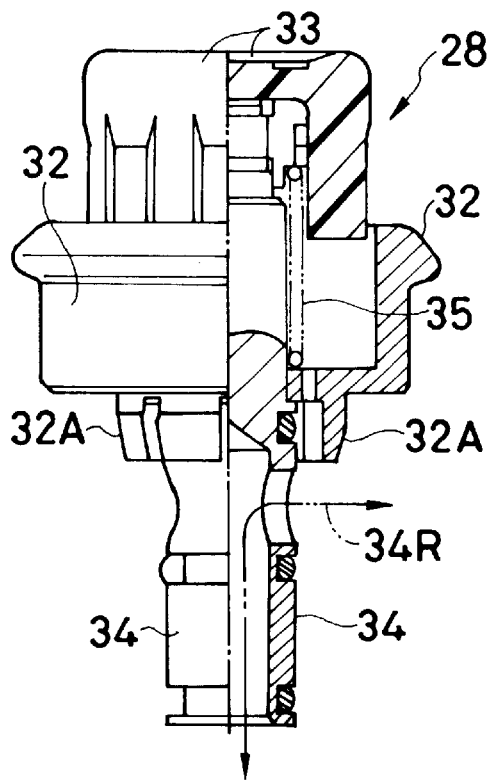
FIG. 1A is a half-face sectional view of a mechanical suction member, showing a configuration of a suction member of an endoscope conduit controller of a first embodiment of the present invention.
Figure 1B:
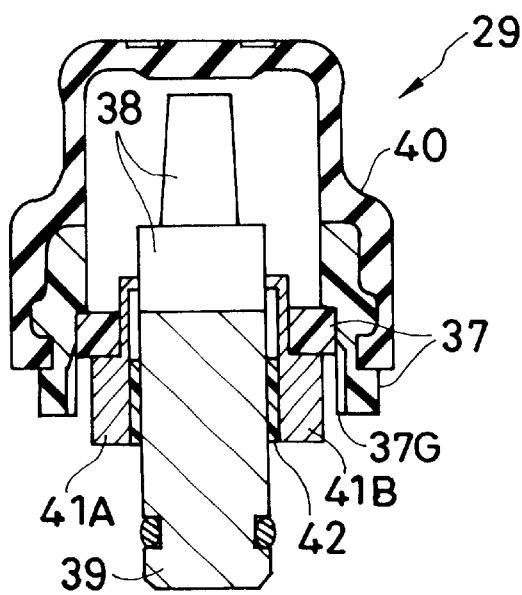
FIG. 1B is a sectional view of an electrical suction member of the first embodiment.
Figure 1C:
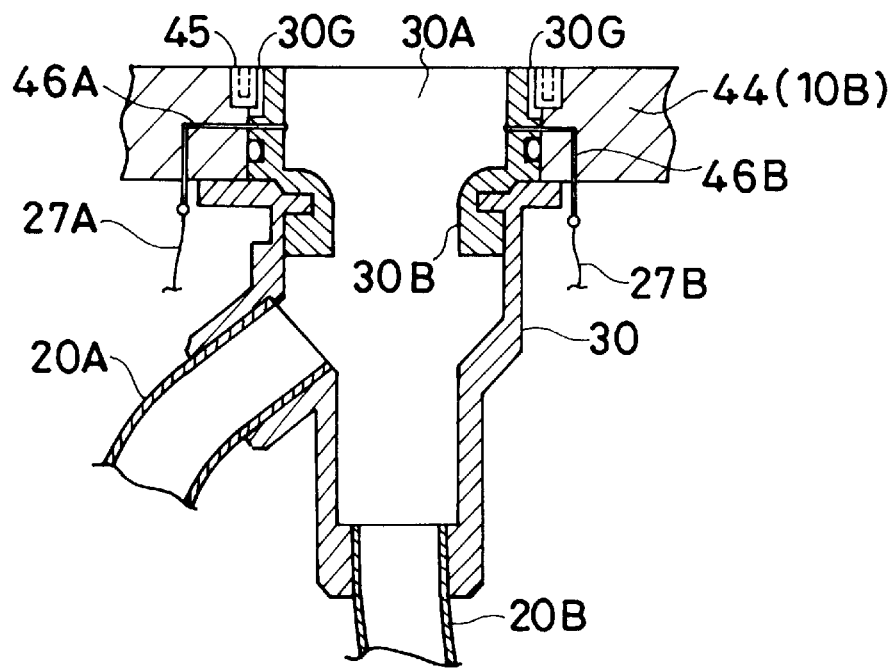
FIG. 1C is a sectional view of a catching part for suction of the first embodiment.

FIGS. 1A to 1C show configurations of a suction member, in which FIG. 1A shows a mechanical suction member 28 (piston part) for a mechanical valve, FIG. 1B shows an electrical suction member 29, and FIG. 1C shows a catching part 30 for suction. First, in case of the mechanical suction member 28, a piston 34 provided with a push button 33 is set to a holding part 32 having a fitting part 32A through a spring 35 so as to be vertically movable and a communication path 34R is provided for the piston 34 as illustrated (by a chain line).

Figure 2:
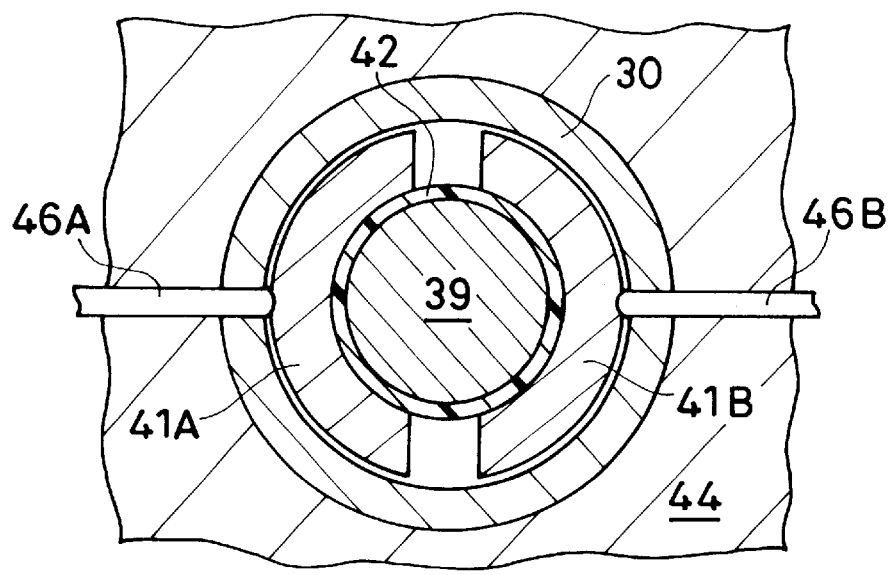
FIG. 2 is a sectional view showing a face of the electrical suction member and the catching part in FIG. 4 obtained by cutting them at a position where an electrode can be seen.

In case of the electrical suction member 29 in FIG. 1B, a cylindrical part 39 having an electrical switch 38 is held by a holding part 37 and covered with a rubber cover 40, and a female screw part 37G is formed inside of the lower part of the holding part 37. As shown in FIG. 2, electrodes 41A and 41B are connected to the switch 38 and set to the periphery of the above cylindrical part 39 through an insulating member 42.

In case of the catching part 30 for suction in FIG. 1C, a male-screw part 30G is formed on the outside of upper part of the part 30 and arranged to a case body 44 of the operation part 10B and then this catching part 30 is set to the case body 44 by screwing a fixing ring (female screw part) 45 to the male-screw part 30G. The fitting part 32A of the operation member 28 is fitted to the catching part 30 and moreover, a catching port 30A for catching the electrodes 41 (A and B) of the operation member 29 is formed and a suction tube 20A extended toward the insertion part 10A and a suction tube 20B extended toward the cable part 10C are arranged on the catching part 30. Furthermore, a fitting wall 30B to which the piston 34 and the cylindrical part 39 are fitted in a watertight state is formed on the part 30. Furthermore, as shown in FIG. 2, electrodes (electric contact points) 46A and 46B are formed so as to pass through the wall of the catching part 30 and slightly protrude beyond the inner wall of the catching port 30A and connected to electrical-signal lines 27A and 27B.

The configuration of the suction part is described above and its action is described below by referring to FIGS. 3 and 4. FIG. 3 shows a state of setting the mechanical suction member 28 {FIG. 1(A)} to the catching part 30 {FIG. 1(B)} (under operation). The suction member 28 is set to the catching part 30 by fitting the fitting part 32A to the catching port 30A. Moreover, in this case, the endoscope 10 (cable part 10C) is connected to the external unit 12 by a connector as shown in FIG. 5.

In FIG. 3, when the push button 33 is not pressed, the upper port (side port) of the communication path 34R is located above the fitting wall 30A. Therefore, the communication path 34R is closed. However, as illustrated, the piston 34 lowers when the push button 34 is pressed and thereby, the communication path 34R is opened. The suction pump operates while the endoscope is used and thereby, contents of an observation object or the like are attracted from the front end of the insertion part 10A. In this case, as understood from FIG. 3. suction magnitudes (suction quantities) can be changed by adjusting a pressed distance of the push button 33 (lowered distance of the piston 34).

FIG. 4 shows a state of setting the electrical suction member 29 {FIG. 1(B)} to the catching part 30. The suction member 29 is set to the catching part 30 by removing the fixing ring 45 from the case body 44, fitting the electrodes 41 (A and B) to the catching port 30A and the cylindrical part 39 to the fitting wall 30B, and screwing the female-screw part 37G of the holding part 37 to the male-screw part 30G on the periphery of the part. In this case, also as shown in FIG. 2, the electrodes 41A and 41B are electrically connected with the electrodes 46A and 46B. Then, in this case, the endoscope 10 (cable 10C) is connected to the solenoid-valve unit 25 shown in FIG. 6 by a connector.

In FIG. 4, when the internal switch 38 is turned off, a solenoid valve for a suction tube in the solenoid-valve unit 25 is closed and the suction tube 20 is closed. However, when the switch 38 is turned on by pressing the upper part of the suction member 29, the solenoid valve is opened by the control part 26 and thereby, contents in an observation object or the like are attracted from the front end of the insertion part 10A. The solenoid-valve unit 25 may be configured so as to be able to control a flow rate. In this case, suction magnitude is adjusted by a switch or the like on the operation panel of the solenoid-valve unit 25. However, because the electrical suction member 29 is not provided with the movable piston 34 having the communication path 34R differently from the case of the mechanical suction member 28, a suction member can be easily cleaned.

Figure 6:
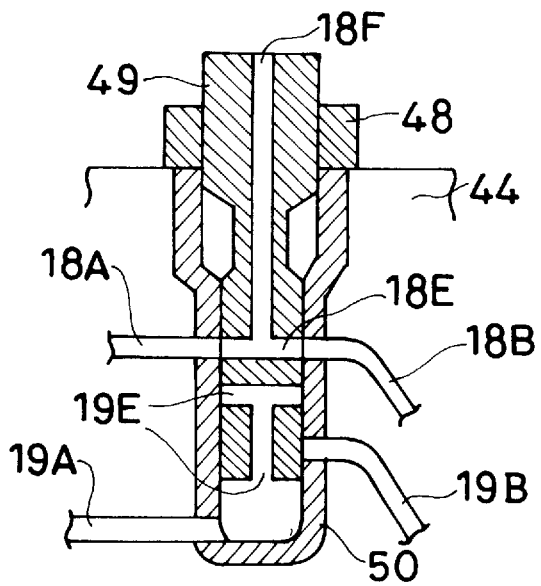
FIG. 6 is an enlarged sectional view of the mechanical air-supply/water-supply operation member in FIG. 5.

Then, the configuration of an air-supply/water-supply member is described below by referring to FIGS. 5 to 7. FIG. 6 shows an enlarged view of a simplified mechanical air-supply/water-supply operation member 48 in FIG. 5. As shown in FIG. 6, a piston 49 on which an air-supply path 18E, an atmosphere-release path 18F, and a water-supply path 19E are formed is set to the air-supply/water-supply operation member 48 through a spring similarly to the case of the suction member 28 so as to be vertically movable for the catching part 50 for air supply/water supply. Front-end-side air-supply tube 18A and water-supply tube 19A and cable-side air-supply tune 18B and water-supply tube 19B are arranged on the catching part 50. As shown in FIG. 5, in the case of the above described mechanical air-supply/water-supply operation member 48, the air supplied by the operation of the pump 14 is exhausted to the atmosphere from the air-supply tube 18 through the atmosphere-release path 18F. When the atmosphere-release path 18F is closed by pressing the upper face of the air-supply/water-supply operation member 48, air is supplied through the air-supply tube 18.

In general, to clean an observation window, by pressing the piston 49 of the air-supply/water-supply operation member 48 while closing the atmosphere-release path 18F on the upper face of the piston 49, the water-supply path 19E is connected to the water-supply tubes 19 (A and B) and water is supplied from the water-supply tank 15 and supplied to the observation window from the front-end nozzle 22 through the water-supply tube 19. Thereafter, by returning the piston 49 upward and closing the upper part of the atmosphere-release path 18F by a finger, air is supplied to the observation window through the air-supply tubes 18 (A and B) in order to remove water.

Figure 7:
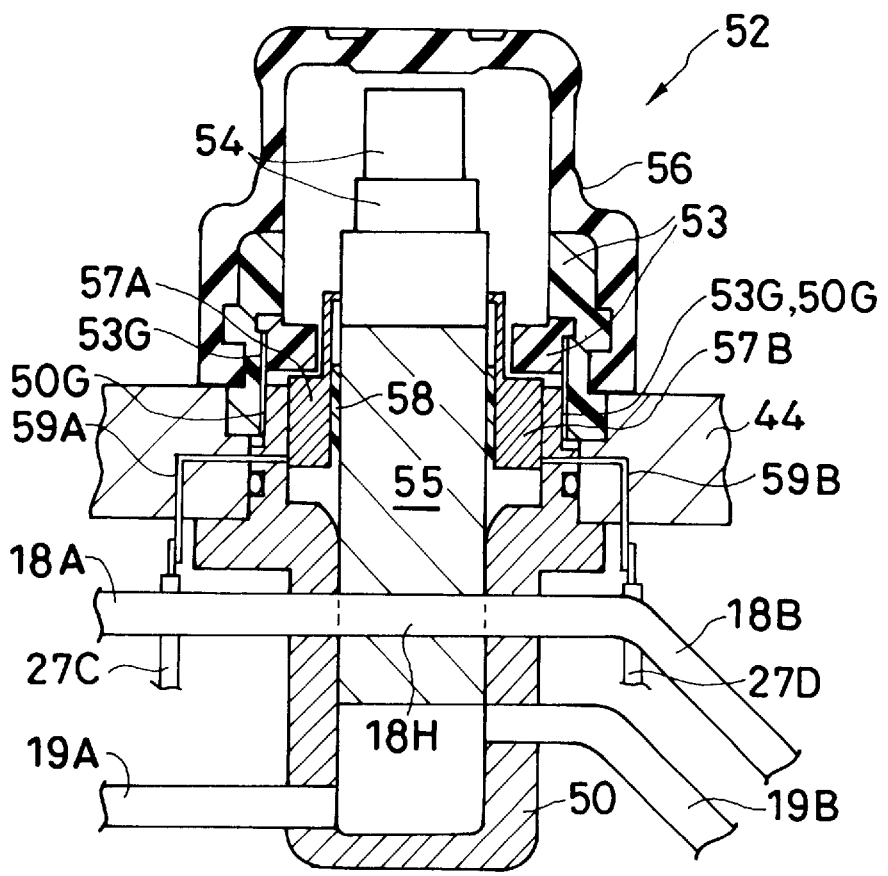
FIG. 7 is a sectional view showing a state of setting the electrical air-supply/water-supply operation member of the first embodiment to a catching part for air supply/water supply.

FIG. 7 shows a state of setting an electrical air-supply/water-supply operation member 52 to the catching part 50 for air supply/water supply. As shown in FIG. 7, in case of the electrical air-supply/water-supply operation member 52, an cylindrical part 55 having a two-stage switch (electrical switch) 54 is held by a holding part 53 and covered with a rubber cover 56, and a male-screw part 53G is formed inside of the lower part of the holding part 53. Electrodes 57A and 57B are connected to the two-stage switch 54 and the electrodes 56A and 56B are set to the periphery of the cylindrical part 55 through an insulating member 58.

Moreover, a male-screw part 50G is formed on the catching part 50 similarly to the case of the suction member, and electrodes 59A and 59B contacting the electrodes 57A and 57B are provided so as to slightly protrude beyond the inner wall and connected to signal lines 27C and 27D. The air-supply tubes 18 (A and B) and the water-supply tubes 19 (A and B) are arranged on the catching part 50 as illustrated. Therefore to connect these tubes 18 and 19, an air-supply path (communication tube) 18H is provided for the cylindrical part 55 of the air-supply/water-supply operation member 52 and the length (bottom height) of the cylindrical part 55 is set to a predetermined value so as to secure a water-supply path.

Moreover, at the time of setting the electrical air-supply/water-supply operation member 52 to the catching part 50, the endoscope 10 (cable 10C) is connected to the solenoid-valve unit 25 as described for FIG. 5. Then, in case of the configuration in FIG. 7, when the internal two-stage switch 54 is turned off, the air-supply solenoid valve and water-supply solenoid valve in the solenoid-valve unit 25 are closed and the air-supply tube 18 and water-supply tube 19 are closed. However, when the first stage of the two-stage switch 54 is turned on by pressing the upper part of the air-supply/water-supply operation member 52, the air-supply solenoid valve is opened by the control part 26 (or it is permitted to open the water-supply solenoid valve), air is supplied from the front-end nozzle 22 of the insertion part 10A toward the observation window through the air-supply tube 18.

On the other hand, when the second stage of the two-stage switch 54 is turned on, the water-supply solenoid valve opens, thereby water is supplied from the water-supply tank 15 through the water-supply tube 19 and discharged from the front-end nozzle 22. There are some controllers configured so as to be able to control a flow rate also in case of the above air supply and water supply. In this case, it is possible to change magnitudes of air supply/water supply by a switch or the like on the operation panel of the solenoid-valve unit 25. Moreover, the electrical air-supply/water-supply operation member 52 can be easily cleaned because it is not provided with the movable piston 34 having complex conduits 18E, 18F, or 19E differently from the case of the mechanical air-supply/water-supply operation member 48.

In case of this embodiment, the fixing ring 45 is removed so as to screw and connect the electrical operation members 29 and 52 each other. However, it is also permitted to set the electrical operation members 29 and 52 to the operation part 10B in accordance with the fitting type similarly to the case of the mechanical operation members 28 and 48 or other connection structure.

Moreover, for this embodiment, a case is described in which the endoscope 10 is connected to the external unit 12 and the solenoid-valve unit 25. However, it is also permitted to use a light-source unit, a processor unit, or a unit obtained by combining the light-source and processor units as the external unit 12 or it is permitted that the solenoid-valve unit 25 is combined with the light-source unit or the like. It is possible to connect the endoscope 10 to various units.

As described above, the first embodiment makes it possible to selectively execute both the fluid control by a mechanical valve and the fluid control by a solenoid-valve unit in one system and properly obtain advantages of the both fluid controls, and secure compatibility between component units produced so as to have control modes different from each other.

Second Embodiment

Figure 10:
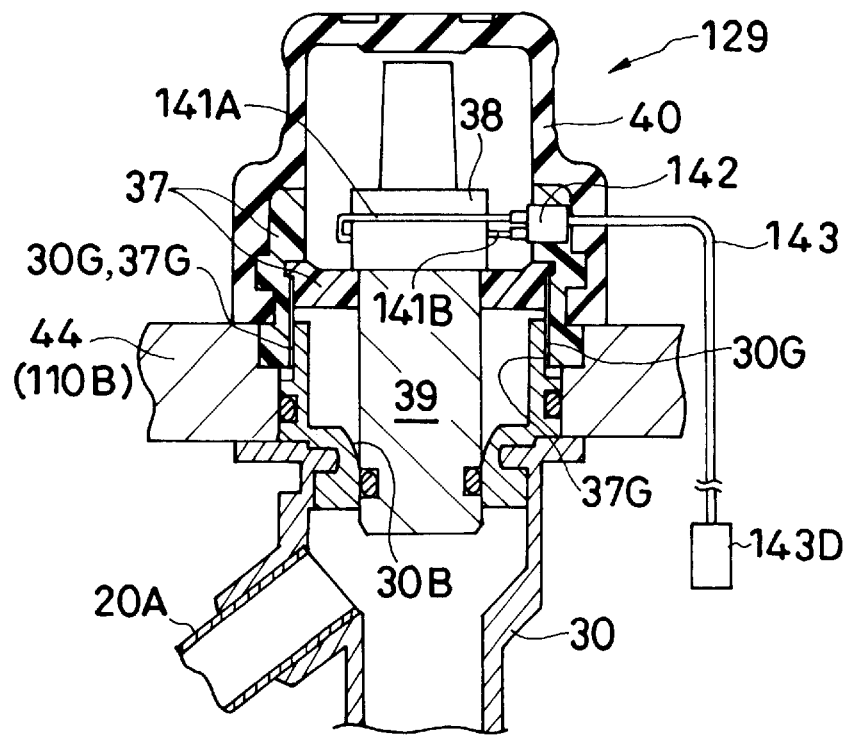
FIG. 10 is a sectional view showing a state of setting the electrical suction member in FIG. 8 to the catching part.
Figure 11:
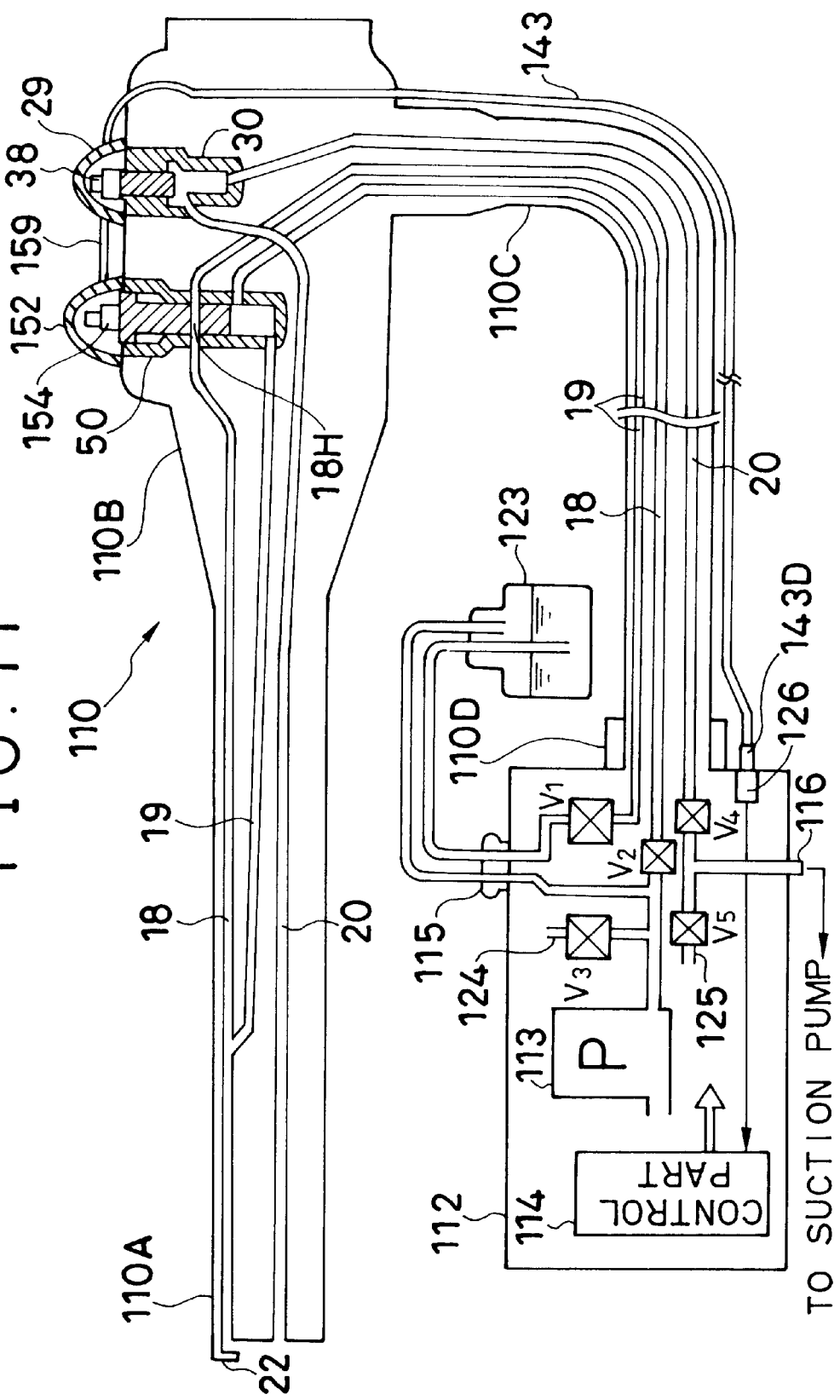
FIG. 11 is an illustration showing the general configuration of the endoscope of the second embodiment at the time of setting an electrical operation member.

FIGS. 8 to 12 show configurations of an endoscope conduit controller of the second embodiment, in which FIG. 11 shows the general configuration of the controller provided with an electrical operation member. In FIG. 11, an endoscope 110 is fabricated by assuming that a mechanical valve is used and configured by an insertion part 110A, an operation part 110B, and a cable part 110C. The cable part 110C is connected to a solenoid-valve unit (fluid supply part) 112. The endoscope 110 also uses an air-supply tube 18, a water-supply tube 19, and a suction tube 20.

The solenoid-valve unit 112 is provided with a pump (air-supply pump) 113, a control part 114, and solenoid valves (including pinch and diaphragm valves) V1 to V5 and connects with a water-supply tank 123 through a connection port 115 and an suction pump through a connection port 116. That is, the solenoid valve V1 is set to the water-supply tube 19, V2 is set to the air-supply tube 18, V3 is set to atmosphere-release tube 124 for the pump 113, V4 is set to the suction tube 20, and V5 is set to an atmosphere-release tube 125 for the suction pump. By opening or closing these solenoid valves V1 to V5 by the control part 114, operations such as air supply, water supply, and suction are executed. Moreover, a connector catching part 126 is set to the solenoid-valve unit 112 in order to input an operation control signal to the control part 114.

Because the endoscope 110 is fabricated so as to be used for a mechanical valve, it is originally set to an external unit (light-source unit, processor unit, or a unit constituted by uniting the above units) having a fluid control part for a mechanical valve. Though the external unit does not have a solenoid valve, it is provided with connection ports for the air-supply pump, water-supply pump, and suction pump shown in FIG. 11.

Moreover, in case of the above endoscope operation part 110B, an electrical operation member (switch) is usably set instead of a mechanical operation member (valve).

Figure 8A:
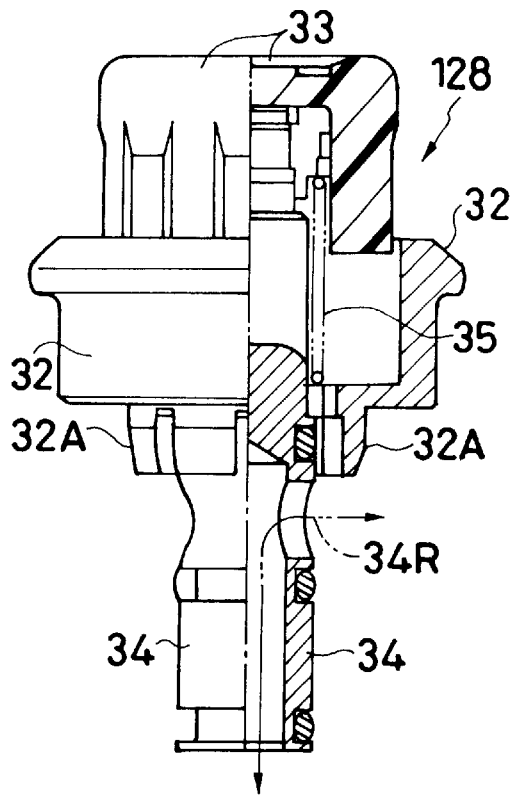
FIG. 8A is a half-face sectional view of a mechanical suction member, showing a configuration of a suction member of an endoscope conduit controller of a second embodiment of the present invention.
Figure 8B:
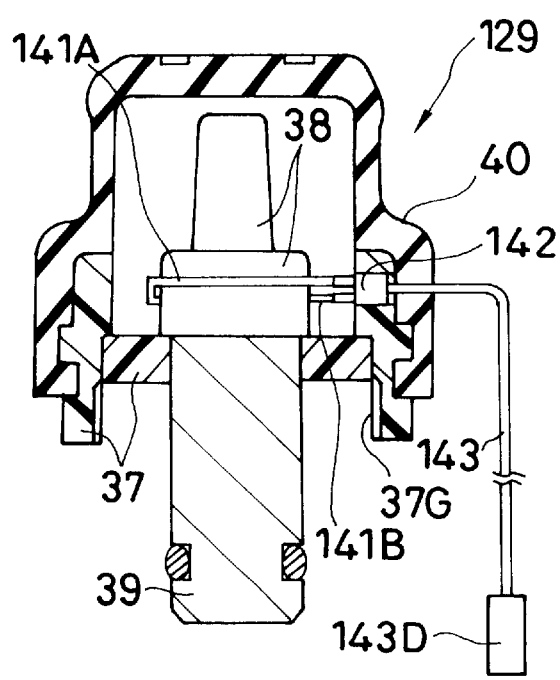
FIG. 8B is a sectional view of an electrical suction member of the second embodiment.
Figure 8C:
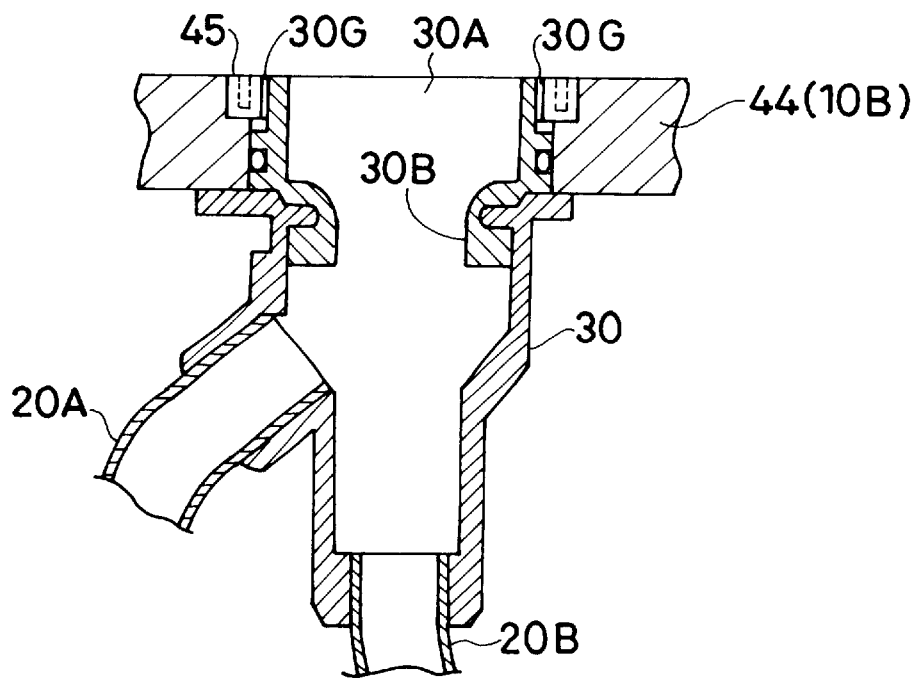
FIG. 8C is a sectional view of a catching part for suction of the second embodiment.
Figure 9:
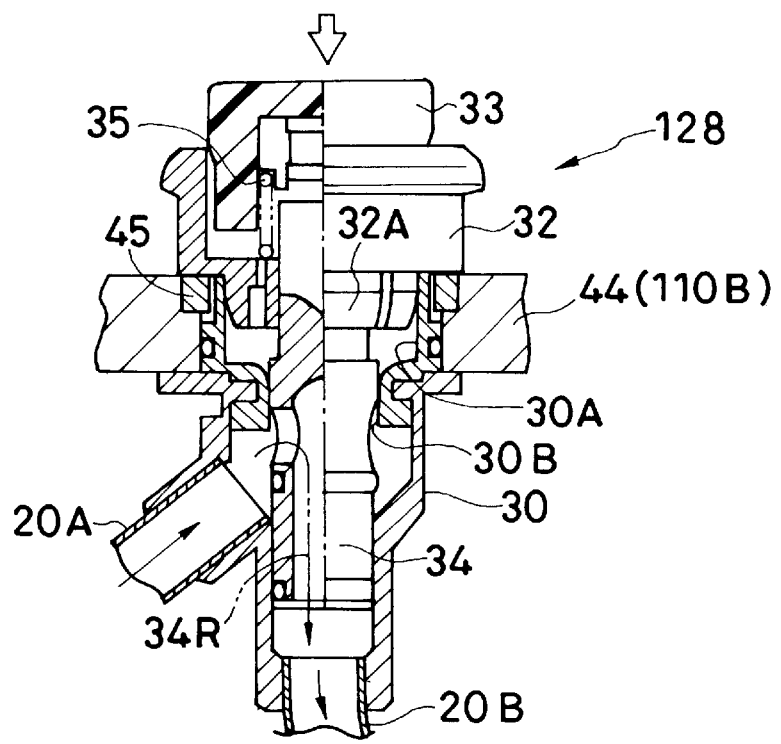
FIG. 9 is a sectional view showing a state of setting the mechanical suction member in FIG. 8 to a catching part (a state of pressing a piston)

FIG. 8A shows a mechanical suction member (piston part) 128 for a mechanical valve, FIG. 8B shows an electrical suction member 129, and FIG. 8C shows a catching part 30 for suction. The configuration of the mechanical suction member 128 in FIG. 8A is the same as the case of the first embodiment.

The electrical suction member 129 in FIG. 8B is basically the same as the case of the first embodiment, in which a cylindrical part 39 having an electrical switch 38 is held by a holding part 37 and covered with a rubber cover 40, and a female-screw part 37G is formed inside of the lower part of the holding part 37. Moreover, an external signal line (electrical-signal cable) 143 is connected to electrodes 141A and 141B of the switch 38 through a joint 142 and a connector 143D to be connected to the connector catching part 126 of the solenoid-valve unit 112 is provided for the front end of the external signal line 143. The external signal line 143 is set along the cable part 110C as shown in FIG. 11.

The catching part 30 for suction in FIG. 8C is basically the same as the case of the first embodiment, in a case body 44 of the operation part 110B this catching port 30 is set to the case body 44 by screwing a fixing ring (screw part) 45 to a male-screw part 30G. A catching port 30A to which a fitting part 32A of the operation member 128 is fitted is formed on the catching part 30 and moreover, a suction tube 20A to an insertion part 10A-side and a suction tube 20B to the cable part 110C are arrange on the part 30. Moreover, a fitting wall 30B to which the piston 34 and the cylindrical part 39 are fitted in a watertight state is formed below the catching port 30A.

The configuration of the suction member is described above. The mechanical suction member 128 is set to the catching part 30 under the state shown in FIG. 9. In this case, the cable part 110C is connected to an external unit having a fluid supply part by a connector. In case of the suction member 128, the piston 34 is lowered by pressing the push button 33 and thereby, the communication path 34R opens and thus, contents of an observation object are attracted from the front end of the insertion part 10A.

FIG. 10 shows a state of removing the mechanical suction member 128 and setting the electrical suction member 129 {FIG. 8(B)} to the catching part 30. The suction member 129 is firmly set to the catching part 30 by removing the fixing ring 45 from the case body 44, fitting the cylindrical part 39 to the fitting wall 30B, and screwing the female-screw part 37G of the holding part 37 to the male-screw part 30G on the periphery of the part. Moreover, as shown in FIG. 11, the cable 11C of the endoscope 110 is connected to the solenoid-valve unit 112 by the connector 110D and the external signal line 143 is connected to the control part 114 in the solenoid-valve unit 112 in accordance with the connection between the connector 143D and the connector catching part 126.

In case of the electrical suction member 129, when the internal switch 38 is turned off, the solenoid valve V4 for suction in the solenoid-valve unit 112 closes, the solenoid valve V5 of the atmosphere-release tube 125 opens, and the suction tube 20 is closed. However, by pressing the upper part of the suction member 29 to turn on the switch 38, the solenoid valve V4 is opened and the valve V5 is closed by the control part 114. Thereby, contents in an observation object or the like are attracted from the front end of the insertion part 110A. The solenoid-valve unit 112 is constituted so as to be able to control a flow rate. In this case, a suction magnitude is adjusted by a switch or the like on the operation panel of the solenoid-valve unit 112. In the case of the electrical suction member 129, a suction member can be easily cleaned because the movable piston 34 having the communication path 34R is not used differently from the case of the mechanical suction member 128.

Then, the configuration of an air-supply/water-supply operation member is described below by referring to FIG. 12. The configuration of a conventional mechanical air-supply/water-supply operation member is the same as that described for FIG. 6, in which air is supplied by closing the upper port of the atmosphere-release path 18F by a finger and water is supplied by pressing the piston 49.

Figure 12:
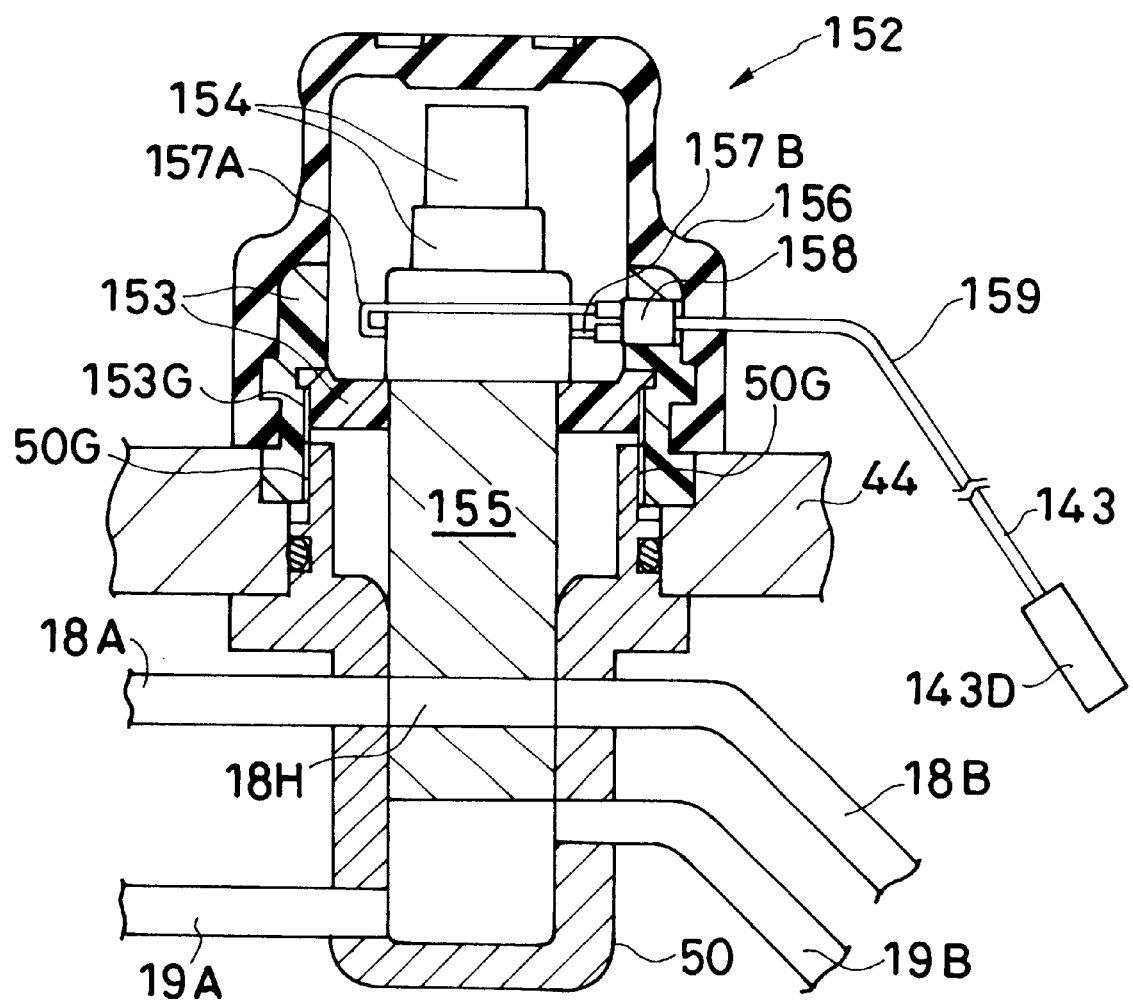
FIG. 12 is a sectional view showing a state of setting the electrical air-supply/water-supply operation member of the second embodiment to a catching part for air supply/water supply.

FIG. 12 shows a state of setting an electrical air-supply/water-supply operation member 152 to the catching part 50 for air supply/water supply. As shown in FIG. 12, in the case of the electrical air-supply/water-supply operation member 152, a cylindrical part 155 having a two-stage switch (electrical switch) 154 is held by a holding part 153 and covered with a rubber cover 156, and a female-screw part 153G is formed inside of the lower part of the holding part 153. An external signal line (electrical-signal cable) 159 is connected to electrodes 157A and 157B of the two-stage switch 154 through a joint 158. The external signal line 159 is united with the external signal line 143 on the way and connected to the solenoid-valve unit 112 from the connector 143D.

On the other hand, the male-screw part 50G is formed on the periphery of the catching part 50 similarly to the case of the suction member and the female-screw 153G of the operation member 152 is screwed to the male-screw part 50G. The air-supply tubes 18 (A and B) and water-supply tubes 19 (A and B) are arranged on the catching part 50 as illustrated. Therefore, to connect these tubes 18 and 19, the air-supply path (communication path) 18H is formed on the cylindrical part 155 of the air-supply/water-supply operation member 152 and the length (bottom height) of the cylindrical part 155 is set to a predetermined value so as to secure a water-supply path.

To connect the electrical air-supply/water-supply operation member 152 to the catching part 50, the endoscope 110 is connected to the solenoid-valve unit 112 as shown in FIG. 11. Then, when the two-stage switch 154 in the electrical air-supply/water-supply operation member 152 is turned off, only the solenoid valve V3 of the atmosphere-release tube 124 opens and the air-supply tube 18 and water-supply tube 19 are closed. However, when the first stage of the two-stage switch 154 is turned on by pressing the upper part of the air-supply/water-supply operation member 152, the solenoid valve V3 is closed by the control part 114 and the solenoid-valve V2 for air supply opens. Thereby, air is supplied to the observation window from the front-end nozzle 22 of the insertion part 110A through the air-supply tube 18.

On the other hand, when the second stage of the two-stage switch 154 is turned on, the solenoid valve V2 closes and the solenoid valve V1 for water supply opens. Thereby, the water in the water-supply tank 123 is supplied from the front-end nozzle 22 through the water-supply tube 19. There are some controllers constituted so as to be able to control a flow rate also in the case of the above air supply/water supply. In this case, it is possible to change magnitudes of air supply/water supply by a switch or the like on the operation panel of the solenoid-valve unit 112.

It is also possible to set the electrical operation members 129 and 152 of the second embodiment to the operation part 110B in accordance with the fitting type similarly to the case of the mechanical operation member 128 or other connection structure.

As described above, the second embodiment makes it possible to use an endoscope using a mechanical valve as an endoscope using a solenoid-valve unit without changing configurations of the former endoscope. Moreover, there are advantages that it is possible to secure the compatibility between the above endoscope and an endoscope produced so as to have a different control mode and there is no waste as equipment or in view of cost.

What is claimed is:

1. A mechanical- and electrical-mode changeable endoscope conduit controller, comprising:

a mechanical operation member for controlling the flow of a fluid in an endoscope conduit in accordance with a mechanical valve configuration;

an electrical operation member for securing the flow of the fluid in the conduit and controlling the flow by an electrical switch;

an operation member catching part on which the conduit is formed and which makes it possible to selectively set or remove both the mechanical operation member and the electrical operation member; and electrical connection means for electrically connecting the electrical switch to the body side when the electrical operation member is set to the operation member catching part.

2. The endoscope conduit controller according to claim 1, wherein the mechanical operation member and the electrical operation member are applied to a suction member for controlling a fluid in a suction tube serving as an endoscope conduit.

3. The endoscope conduit controller according to claim 1, wherein the mechanical operation member and the electrical operation member are applied to an air-supply/water-supply operation member for controlling fluids in an air-supply tube and a water-supply tube serving as endoscope conduits.

4. An endoscope conduit controller, comprising:

a mechanical operation member for controlling the flow of a fluid in an endoscope conduit in accordance with a mechanical valve configuration;

a catching part to which the mechanical operation member is removable fitted and on which the conduit is set;

an electrical operation member which is configured so as to be removable from the catching part and which secures the flow of the fluid in the conduit and controls the flow with an electrical switch; and signal transmission means for inputting an operation signal of the electrical operation member to an electrical fluid supply part through the outside of an endoscope.

5. The endoscope conduit controller according to claim 4, wherein the mechanical operation member and the electrical operation member are applied to a suction member for controlling a fluid in a suction tube serving as an endoscope conduit.

6. The endoscope conduit controller according to claim 4, wherein the mechanical operation member and electrical operation member are applied to an air-supply/water-supply operation member for controlling fluids in an air-supply tube and a water-supply tube serving as endoscope conduits.

* * * * *